United States Patent
Previdi et al.

(10) Patent No.: US 9,346,515 B2
(45) Date of Patent: May 24, 2016

(54) PEDAL ASSISTED BICYCLE AND METHOD OF CONTROLLING THE PEDAL ASSISTED BICYCLE

(71) Applicants: Politecnico di Milano, Milan (IT); Università degli Studi di Bergamo, Bergamo (IT)

(72) Inventors: Fabio Previdi, Milan (IT); Sergio Matteo Savaresi, Cremona (IT); Matteo Corno, Milan (IT); Mara Tanelli, Lodi (IT); Giovanni Alli, Legnano (IT); Paolo Lisanti, Lallio (IT); Pierfrancesco Spagnol, Milan (IT); Ivo Boniolo, Bovisio Masciago (IT); Cristiano Spelta, Bellusco (IT)

(73) Assignees: Politecnico di Milano, Milan (IT); Università degli Studi di Bergamo, Bergamo (IT)

( * ) Notice: Subject to any disclaimer, the term of this patent is extended or adjusted under 35 U.S.C. 154(b) by 0 days.

(21) Appl. No.: 14/375,844

(22) PCT Filed: Feb. 13, 2013

(86) PCT No.: PCT/IB2013/051154
§ 371 (c)(1),
(2) Date: Jul. 31, 2014

(87) PCT Pub. No.: WO2013/124764
PCT Pub. Date: Aug. 29, 2013

(65) Prior Publication Data
US 2015/0019062 A1    Jan. 15, 2015

(30) Foreign Application Priority Data

Feb. 22, 2012  (IT) ............................. MI2012A0260

(51) Int. Cl.
*B62M 6/40* (2010.01)
*B62M 6/45* (2010.01)
(Continued)

(52) U.S. Cl.
CPC ................. *B62M 6/50* (2013.01); *A61B 5/024* (2013.01); *B60L 7/12* (2013.01); *B60L 11/007* (2013.01);
(Continued)

(58) Field of Classification Search
CPC .............................. B62M 6/50; B60L 11/007
See application file for complete search history.

(56) References Cited

U.S. PATENT DOCUMENTS

2005/0246152 A1   11/2005   Kokatsu et al.
2008/0071436 A1    3/2008   Dube
(Continued)

FOREIGN PATENT DOCUMENTS

DE           19732468 A1      6/1998
DE         102007050552 B3     9/2008
EP            1295785 A1      3/2003

OTHER PUBLICATIONS

International Search Report & Written Opinion in PCT/IB2013/051154 dated Jun. 20, 2013.

*Primary Examiner* — Todd Melton
(74) *Attorney, Agent, or Firm* — Manelli Selter PLLC; Edward J. Stemberger

(57) ABSTRACT

A pedal assisted bicycle a first and a second wheel; a pedaling assembly mechanically decoupled from the first and second wheels by which an user can supply a pedaling power; an electric motor mechanically coupled to at least one of the wheels capable of taking a motor power; a generator device adapted to generate a generator device electric power from the pedaling power, arranged in an energy exchange relationship with the pedaling assembly and the electric motor; an energy storage device arranged in an energy exchange relationship with the electric motor and with the generator device; a control system including a module for controlling the power required to the generator device to be supplied to the electric motor and/or to the storage device; a heartbeat sensor adapted to generate a signal representing heartbeat.

22 Claims, 3 Drawing Sheets

(51) Int. Cl.
| | |
|---|---|
| *B62M 6/50* | (2010.01) |
| *B62M 6/60* | (2010.01) |
| *B60L 11/00* | (2006.01) |
| *B60L 7/12* | (2006.01) |
| *B60L 11/18* | (2006.01) |
| *B60L 15/20* | (2006.01) |
| *A61B 5/024* | (2006.01) |
| *B62K 11/00* | (2006.01) |
| *B62M 6/90* | (2010.01) |
| *G01P 3/44* | (2006.01) |
| *B62J 99/00* | (2009.01) |

(52) U.S. Cl.
CPC ......... *B60L 11/1805* (2013.01); *B60L 11/1861* (2013.01); *B60L 11/1877* (2013.01); *B60L 15/2009* (2013.01); *B60L 15/2072* (2013.01); *B62K 11/00* (2013.01); *B62M 6/40* (2013.01); *B62M 6/45* (2013.01); *B62M 6/60* (2013.01); *B62M 6/90* (2013.01); *G01P 3/44* (2013.01); *B60L 2200/12* (2013.01); *B60L 2220/44* (2013.01); *B60L 2240/12* (2013.01); *B60L 2240/429* (2013.01); *B60L 2240/642* (2013.01); *B60L 2250/12* (2013.01); *B60L 2250/24* (2013.01); *B62J 2099/002* (2013.01); *B62J 2099/0026* (2013.01); *Y02T 10/642* (2013.01); *Y02T 10/705* (2013.01); *Y02T 10/7005* (2013.01); *Y02T 10/7044* (2013.01); *Y02T 10/7275* (2013.01); *Y02T 10/7291* (2013.01); *Y02T 90/16* (2013.01)

(56) References Cited

U.S. PATENT DOCUMENTS

| | | |
|---|---|---|
| 2009/0181826 A1 | 7/2009 | Turner |
| 2011/0266082 A1 | 11/2011 | Yang |
| 2012/0029744 A1 | 2/2012 | Yun |
| 2012/0202649 A1* | 8/2012 | Huber .................. A63B 69/16 482/2 |

* cited by examiner

1

PEDAL ASSISTED BICYCLE AND METHOD OF CONTROLLING THE PEDAL ASSISTED BICYCLE

TECHNICAL FIELD OF INVENTION

The object of the present invention is a pedal assisted bicycle without chain between pedals and driving wheel. The object of the present invention is also a method of controlling the bicycle itself.

PRIOR ART

Different types of pedal assisted bicycles are known.

According to a first type, a normal bicycle with a chain is equipped with an electric motor to assist pedaling. According to this type of bicycle, the power required to move bicycle is supplied to the driving wheel at the same time by the user via chain and by the motor.

A second type of bicycle known provides the total mechanical decoupling between pedals and driving wheel, which therefore are not connected together by a chain. The pedaling activates an electrical generator, which in turn provides an electric motor with the electrical power required to move the bicycle. A battery provides also a surplus of power to the motor in predetermined circumstances. Such a battery can for example be activated by the activation of a button by the user.

The first type of bicycle is structurally complicated because its moving is obtained by combining energy sources of different nature that act in parallel i.e. the user himself and the motor.

The second type of bicycle is structurally simpler because the driving wheel is moved exclusively by the electric motor but it is complex from the control point of view. In fact, the control algorithms so far proposed to adjust the surplus of power supplied from the battery as well as the power required to the generator are still rather rudimentary. In particular, such algorithms are not able to manage the power flows in such a way to relieve the user effort in a controlled way, for example, after a long journey.

SUMMARY OF THE INVENTION

The object of the present invention is therefore to make available a pedal assisted bicycle structurally simple and able to keep under control the user effort.

This and other objects are achieved by a pedal assisted bicycle according to claim 1 and a method of controlling a pedal assisted bicycle according to claim 13.

BRIEF DESCRIPTION OF THE FIGURES

To better understand the invention and to appreciate its advantages some exemplary non-limiting embodiments will be described below with reference to the attached Figures wherein.

DETAILED DESCRIPTION OF THE INVENTION

Figure 1:
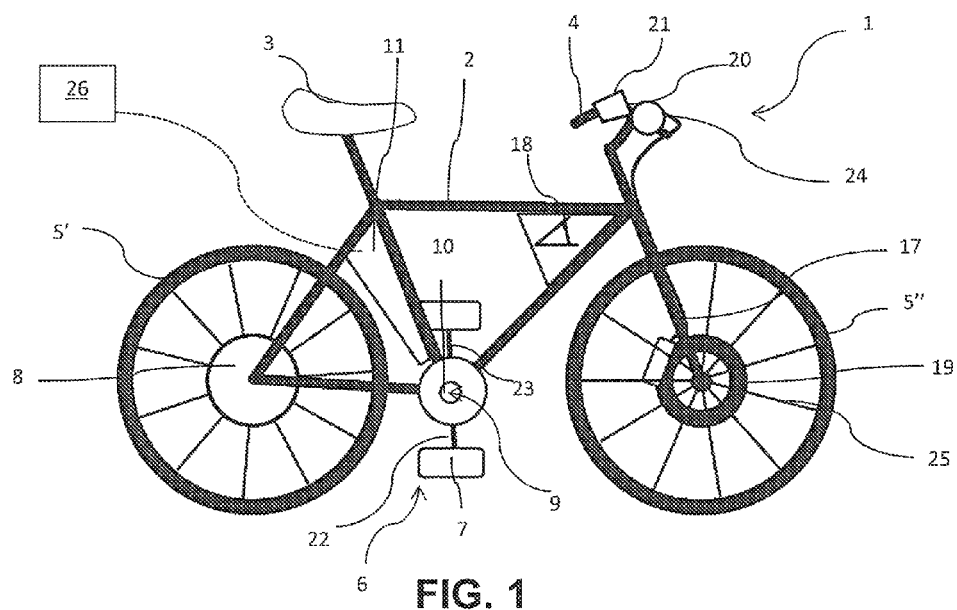
FIG. 1 is a schematic side view of a bicycle according to the invention.

With reference to the attached Figures, in FIG. 1 is shown schematically a pedal assisted bicycle, indicated by the reference 1. The bicycle 1 comprises some components normally present in standard bicycle, i.e. with mechanical transmission. In particular, bicycle 1 comprises, for example, a frame 2, a seat 3, handlebars 4. Bicycle 1 further comprises a first 5' and a second 5" wheel connected with the frame 2. For example, the first wheel 5' is the rear wheel and the second wheel 5" is the front wheel, with reference to a normal advancing direction of the bicycle itself.

Bicycle 1 comprises a pedaling assembly 6, provided with pedals 7 through which the user can move the pedaling assembly itself 6 producing a pedaling power Wped.

Contrary to what happens in standard bicycle, the pedaling assembly 7 is mechanically decoupled from the wheels 5' and 5". In other words, between pedaling group 6 and wheels 5' and 5" there is no mechanical transmission such as, for example, a chain or a cardan movement.

Bicycle 1 comprises an electric motor 8 mechanically coupled to one of the two wheels 5' and 5". Preferably, the electric motor 8 is associated to the rear wheel 5'. The connection between the drive shaft of the motor (not shown in the Figures) and the driving wheel of the bicycle is preferably direct, in such a way that an integrated rotation of the wheel 5' corresponds to a rotation of the electric motor 8. The electric motor 8 must be powered electrically for its functioning, in such a way which will be explained later. When the motor 8 is powered, it absorbs a motor power Wmot.

Bicycle 1 comprises also an electric power generator device 9 placed in a connection of energy exchange with the pedaling assembly 6 and with electric motor 8. In particular, advantageously, the generator device 9 is connected mechanically to the pedaling assembly 6 so as to convert the mechanical pedaling power Wped into electric power. Such electric power is supplied, at least in part, to the electric motor 8. Preferably, the generator device 9 comprises an electric generator such as, for example, an induction generator. According to this exemplary embodiment a rotation of the rotor of the generator corresponds to the rotation of the pedaling assembly 6. The generator device 9 is able to provide a generator device electric power Wgen, which, as it will be seen, is the object of the control in the bicycle according to the invention.

Since the generator device 9 is placed in connection with pedaling assembly 6 and converts mechanical energy provided by the user into electric energy, it determines the resisting torque encountered by the user during pedaling. Modifying operating parameters of the generator device, the current for example, it can therefore change the power of the generator device and also the resisting torque encountered by the user.

Bicycle 1 comprises also an energy storage device 10, for example one or more batteries. The energy storage device 10 is placed in an energy exchange connection with both the electric motor 8, with both the generator device 9, so as to be able to exchange power with them.

Figure 2:
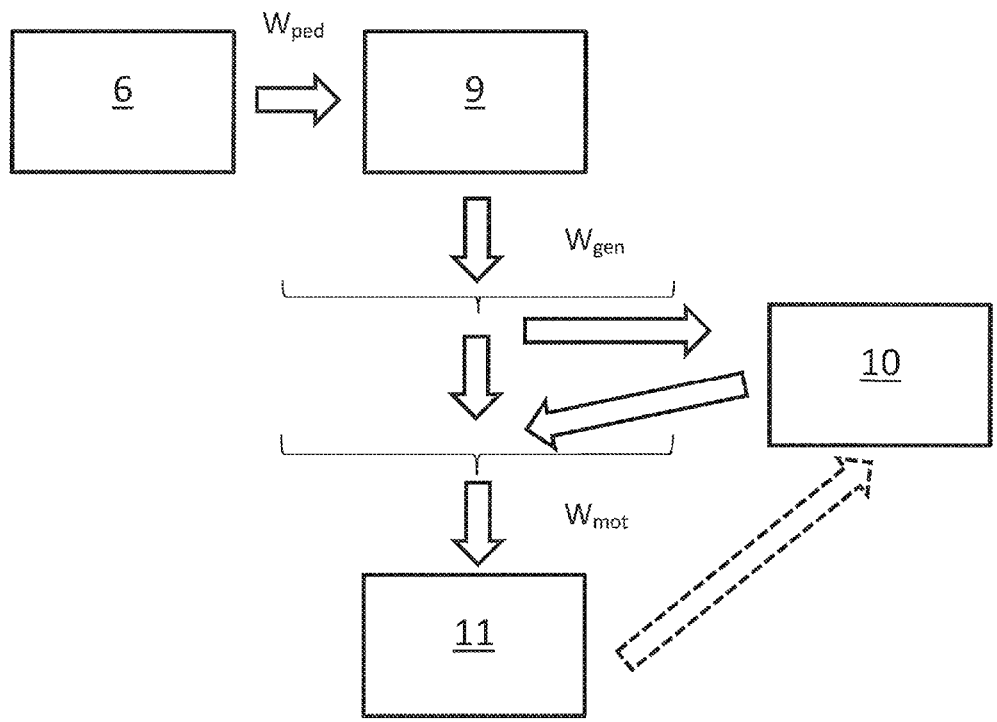
FIG. 2 is a schematic view of the flows of the powers involved in the functioning of the bicycle according to the invention.

With reference to FIG. 2, the power flows provided in the bicycle 1 will now be described.

When the user pedals, he introduces a mechanical pedaling power Wped through the pedaling assembly.

This power is converted into electric power by the generator device 9.

In order to determine the required power to the generator device, from which, as said, depends the resisting torque, which opposes the user pedaling, the bicycle comprises a control system (shown schematically in the Figures with reference number 11), which comprises a module for controlling the electric power required to the generator Wgen. The latter is set by a control algorithm, which will be described later.

The control system further comprises, advantageously, a module for controlling the electric module such that the bicycle 1 moves according to a predetermined law, preferably adjustable by the user. For example, it is possible to impose a predetermined law speed. In this case it is possible to control in closed-loop the motor in known ways. Alternatively it is possible to set the power or the supply current of the motor.

The power provided by the generator device Wgen goes in part to the motor 8 and, in certain circumstances, can go at least in part to the storage device 10. This situation occurs, for example, in the case in which the power required to the motor Wmot is less than the power required to the generator device Wgen. In this case, the power surplus supplied by the generator device 9 is sent to the storage device 10, which therefore is recharged.

In the case in which the power required to the motor Wmot is equal to the power required to the generator device Wgen, the storage device 10 preferably does not exchange power neither with the generator device 9, nor with the motor 8.

In the case, instead, in which the power required to the motor Wmot is higher than the power required to the generator device Wgen, the missing power surplus is made available to the motor 8 from the storage device 10.

It is also possible the case in which the motor 8 recharges the storage device 10 (dashed arrow in FIG. 10), i.e. the case in which the motor power is negative, i.e. incoming and therefore not driving. This situation occurs, for example, in the case in which the bicycle drives along a downhill path.

Advantageously, the bicycle 1 comprises a heartbeat sensor 26, able to detect the user's heartbeat during the use of the bicycle 1. Such a heartbeat sensor 26 may be of different types. For example, it may be in the form of known medical probe type to be applied on the user's body. Alternatively, it may be incorporated in a wrist bracelet, in a watch, in a ring or in a mobile phone. According to a further option, the heartbeat sensor is included within a heart stripe. The heartbeat sensor is able to generate a signal representing the heartbeat detected.

The module for controlling the power required to the generator device Wgen is operatively connected to the heartbeat sensor 26. This connection is preferably wireless mode. The module for controlling the power Wgen required to the generator device is configured in such a way as to determine the electric power required to the generator device as function of the signal representing the heartbeat.

The control system configured in this way controls the user's effort and, acting on the power required to the generator device, also acts on the resisting torque, which opposes pedaling of the latter. Therefore, it is possible to influence the user's effort during the use of the bicycle. In the exemplary case in which the control system determines an excessive user's effort, the power required to the generator device Wgen is reduced and the possible power deficit may be supplied from the storage device, if it is necessary. If on the contrary the user is striving too little, the control system makes sure that the power required to the generator device is increased and, therefore, that the resisting torque increases. If the power required to the generator device Wgen is excessive compared to the power required by the motor Wmot, the power excess will be used to recharge the storage device 10.

The modalities with which the power required to the generator device 9 is measured on the basis of the heartbeat may be various. Preferably the user can set his favorite mode for a particular use of the bicycle 1.

Figure 3:
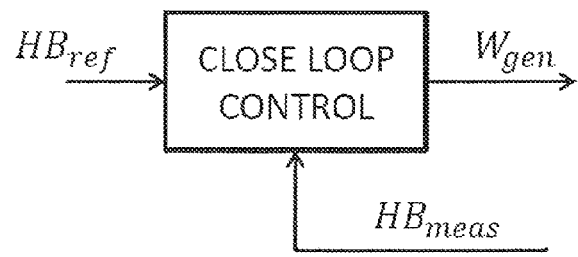
FIG. 3 is a block diagram representative of a method of controlling the bicycle according to a possible embodiment.

According to a possible embodiment, in the control system, a predetermined heartbeat pattern reference is set and, depending on the actual heartbeat measured through the heartbeat sensor 26, a closed-loop control is performed of the error between the reference heartbeat and the actual heartbeat. Modifying the power required to the generator (and, therefore, the resisting torque) the heartbeat error is controlled. This control mode is shown schematically in FIG. 3.

For example, for controlling the heartbeat error, it is possible to use conventional controllers such as P, PD, PI, or PID, or different nature controllers, for example fuzzy logic controllers.

According to a possible example, the profile of the heartbeat reference is a constant profile, i.e. a number of heartbeats constant per time unit. This constant number of heartbeats per time unit may be chosen by the user, according as he wants to make a minimum effort (for example not to sweat) or a high effort (for example to perform a heavy physical activity). If an actual heartbeat higher than a predetermined heartbeat is detected, the control system operates on the power required to the generator device Wgen, reducing it, so as to reduce also the user's effort and so as to slow down the heartbeat.

If, vice-versa, a heartbeat is detected too slow compared to the reference profile, the control system provides to increase the power requested to the generator device.

Of course, it is possible to use heartbeats profiles different from which indicated above, that is constant. For example, a decreasing profile of heartbeat can be provided, so as to concentrate the effort in the initial part of the path, or increasing, so as to concentrate the effort in the final part of the path. It is also possible to modify the reference heartbeat profile during the motion, for example, in the case in which the user is excessively tired and no longer able to continue pedaling with the modalities originally set.

Figure 4:
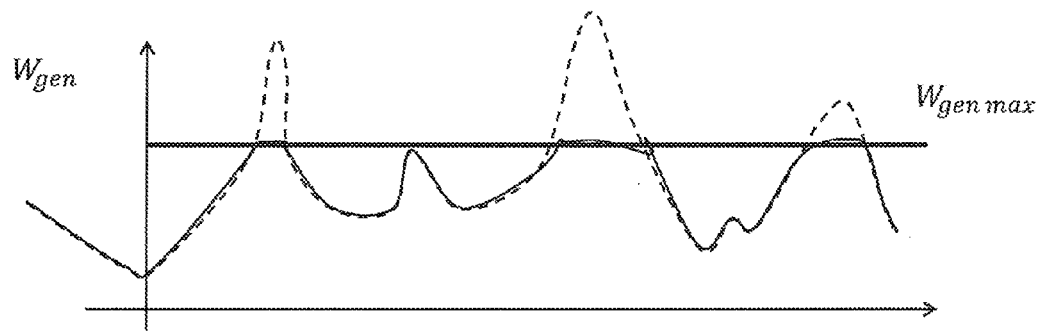
FIG. 4 is a diagram illustrative of a method of controlling the bicycle according to a possible embodiment.

According to a possible embodiment, the module for controlling the electric power required to the generator device Wgen comprises a suitable filter to limit the latter, keeping it below a predetermined maximum value. The effect due to the presence of this filter is shown in FIG. 4, in which it is shown how the power peaks required to the generator device Wgen, higher than the maximum value set Wgen max, are cut. In this way, the effort peaks to which the user is subjected are also eliminated, the user can, therefore, maintain an effort profile, i.e. of the heartbeat, sufficiently uniform.

According to a possible embodiment, the module for controlling the power required to the generator device is configured in such a way as to correct the power required to the generator device Wgen depending on the actual amount of energy available in the storage device 10. In particular, the power required to the generator device Wgen is determined as function of the charge of the batteries, as well as a driving range preset of the bicycle, for example set by the user.

Figure 5:
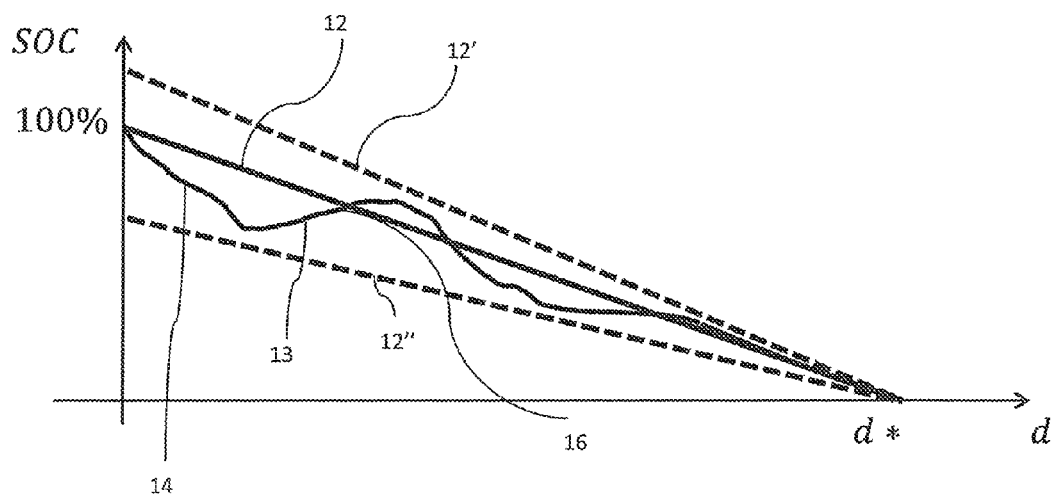
FIG. 5 is a diagram illustrative of a method of controlling the bicycle according to a further possible embodiment.

The situation is schematically shown in the diagram in FIG. 5.

The abscissa shows the distance traveled by the vehicle (d) and the ordinate shows the charge value of the storage device (SOC), which can reach a maximum of 100%. Reference 12 indicates a theoretical profile of desired charge, assuming that the storage device is completely exhaust once the bicycle traveled a maximum distance desired d*. In FIG. 5, this charging profile has a linear course, but charging profiles with different trend are also possible.

In order that the bicycle succeeds in driving the set distance d*, the control system makes sure that the effective charge of the storage device (shown in FIG. 5 with the curve 13) varies around the theoretical charge value remaining between two limit values top and bottom (respectively indicated with the dashed lines 12' and 12"). To do this, the control system acts on the power required to the generator device Wgen, possible modifying the determined value according to the previously described heartbeat control.

The section indicated with 14 of the real charge profile 13 is a high performance section, for example a section in which a high power is required to the motor. In this section, if the power required to the generator device Wgen is not sufficient to ensure the required power level to the motor, the storage device occurs, which provides the missing power portion. The storage device, therefore, discharges and its charge SOC decreases.

The section indicated with 16 of the real charge profile 13 is instead a low-power section, for example, a section in which a low power is required to the motor, or in any case a motor power lower than the power required to the generator device. In these circumstances, the power in excess required to the generator device serves to recharge the storage device, whose charge, therefore, grows.

For the purpose of operating the modalities of control above described, the bicycle is advantageously provided with a sensor 25 suitable for measuring the distance traveled by the bicycle (for example, it is possible to provide a sensor able to measuring the rotations number of one of the bicycle wheels since the start of the bicycle itself, from which it is immediate to obtain the distance traveled by the bicycle). The signal of the sensor for detecting the distance 25 is sent to the module for controlling the power required to the generator. Furthermore the control system comprises, advantageously, a module for monitoring the energy amount of the storage device in particular of the charge of the storage device. The sensor for detecting the distance 25 and the module for monitoring the energy amount of the storage device are operatively connected to the module for controlling the power required to the generator device.

Advantageously, the bicycle 1 comprises a sensor 17 for detecting the speed of the bicycle itself, suitable to generate a signal representing such a speed. Such a sensor 17 can be of different types. For example, speed can be derived from a displacement sensor, such as, for example, the displacement sensor 25 of the type previously identified.

Bicycle speed detecting sensor 17 can find various applications in the bicycle according to the invention, in particular in relation to the determination of the power required to the generator device Wgen.

According to a possible embodiment, bicycle speed detecting sensor 17 can be used to simulate the aerodynamic resistance of the bicycle, which as it is known, increases with the square of the speed. For this purpose, the power required to the generator device, determined in the ways so far said, can be corrected by adding a proportional term to the vehicle speed to square. In this regard see FIG. 6 that shows a possible correction of the power required to the generator device Wgen as a function of the vehicle speed $v_{veh}$. The contribution of this corrective term of the power required to the generator device can be accentuated or limited by acting on an adjustment parameter $\beta$, selectable by the user.

In order to realize this type of correction of the power required to the generator device, the module for controlling the power required to the generator device is advantageously operatively connected to bicycle speed detecting sensor 17 and configured so as to determine the electric power required to the generator device also as a function of bicycle speed representing signal, originated by such a speed sensor 17.

According to a further possible embodiment, the bicycle speed-detecting sensor is used to determine a corrective term of the power required to the generator device that simulates the vehicle inertia, which, as known, shows as resisting force in the event of a vehicle acceleration, or, vice-versa, as driving force in the event of a deceleration. The power required to the generator device can therefore be corrected with a function term of the speed variation per unit time such as the following: $(v2-v1)(t2-t1)$, wherein v and t respectively indicate the vehicle speed and the considered instant of time, measured in two different instants.

Preferably the above mentioned term of correction related to the vehicle inertia can be further corrected with a term which is a part of the power absorbed by the motor Wmot, such as a term $\alpha$Wmot, where $\alpha$ is a coefficient less than 1 which can be modified by the user and possibly be set equal to 0.

According to a further possible embodiment, the bicycle 1 comprises a sensor 18 for detecting the path slope along which the bicycle is running. Such a path slope detecting sensor 18 is suitable for generating a signal representing the path slope and it is operatively connected to the module for controlling the power required to the generator device Wgen. In this way, the latter is able to correct the power required to the generator device, determined in the ways said so far, with a further term which considers the additional effort required to the use due to the path slop. Furthermore, the path slope detecting sensor 18 can be used to detect the condition of the negative slope, i.e. of a downhill path, by the bicycle, condition in which it is possible to recover the kinetic energy. In fact, in this circumstance, the motor does not deliver power but acts as a brake. In other words, the energy is going into the system. Such energy can be stored, for example, in the storage device 10. Such a situation is shown in FIG. 2, where the dotted arrow shows exactly the power flows from the motor 8 to the storage device in such a circumstance.

For example, in the case in which the bicycle is in a rising path, it is possible to increase the power required to the generator, while in a downhill path this power can be reduced up to possibly be cancelled.

The user carries out the modality of energy recovering, during a downhill path travel described above, preferably in the presence of a braking action.

In this regard, the bicycle 1 comprises preferably at least one mechanical brake 19, of a type per se known, applied on one or both the rear 5' and the front 5" wheels. For example, the mechanical brake 19 may be of the lever type, the disk type, or the brake dump type. The user through a brake command such as for example a knob 20 actuates the brake 19.

Advantageously, bicycle 1 comprises a sensor 21 for detecting braking intent of the user. For example, such as sensor 21 may be connected to the knob 20, so as to detect the braking intent of the user. Such a sensor, in this circumstance, generates a signal representing the braking intent of the user that is sent to the control system to which the sensor 20 is operatively connected. In this way, the control system as function of the absence or presence of braking by the user, can act suitably on the motor power Wmot (through the module for controlling the motor power) and the power required to the generator device Wgen, as it will described shortly.

With a further advantage, the bicycle 1 comprises a sensor 22 for detecting pedaling assembly speed 6 suitable to generate a signal representing the pedaling speed to be sent to the control system, in particular to the module for controlling the electric motor and the module for controlling the power required to the generator device. For example, the sensor 22 can comprise a position/angular speed sensor such as for example a speed sensor of the inductive type, or a digital sensor such as a tachymeter encoder.

Figure 7:
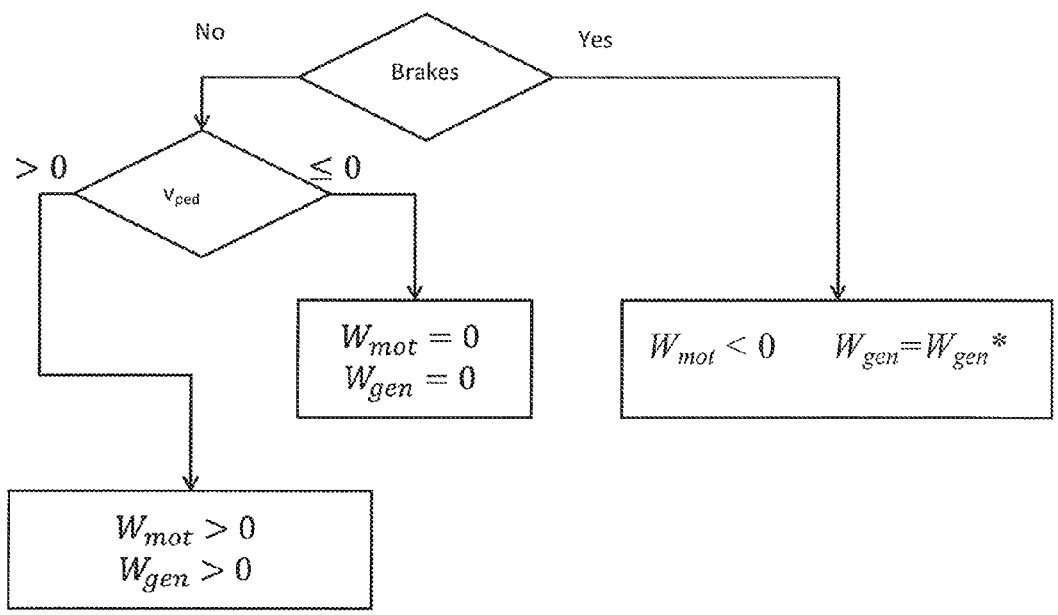
FIG. 7 is a block diagram representative of a method of controlling the bicycle according to a further possible embodiment.

A possible logic of control based on the braking intent of the user and on the pedaling speed is shown schematically in FIG. 7.

Going into details of what has been shown in FIG. 7, in absence of a braking command by the user (Brakes=no) two different situations can occur:

1) The user pedals with a positive speed ($v_{ped}$>0), i.e. he pedals in a direction that in a conventional bicycle mechanical transmission causes the advancement of the bicycle of itself;
2) The user does not pedal (the pedaling speed is equal to 0, $v_{ped}$=0), or he pedals backwards (negative pedaling speed, $v_{ped}$=0).

The situation 1) corresponds to the condition of forward motion of the bicycle. Therefore, the control system determines the motor power Wmot and the power required to the generator device Wgen in the ways already described.

In the case 2), instead, since the user does not pedal, ore pedals backwards, the pulling power of the bicycle stops, and thus both the power required to the generator device Wgen, and the motor power Wmot are maintained as zero. Alternatively, the motor power Wmot may be maintained negative, i.e. it can make sure that the motor acts as brake.

In the case in which the brake command is activated (Brakes=yes), the electric motor is used as a brake. In other words, the power flows is incoming and can be used, for example, to recharge the storage device. Depending on the type of the electric motor used, the motor itself can function as generator to provide power to the storage device ore alternatively it can be used as an additional electric generator. The power required to the generator device Wgen is in this case preferably maintained at a minimum predetermined level Wgen*, so that the user still notices a minimal resistance to pedal.

The above mentioned energy recovery can possibly be realized even in the absence of braking when the sensor 18 for detecting the slope detects that the bicycle is moving downhill.

Advantageously, the bicycle 1 comprises a sensor 24 for detecting the user intent of operating bicycle. Such a sensor 24 is operatively connected to the control system, in particular to the module for controlling the electric motor and to the module for controlling the power required to the generator device, and is suitable to send them a signal representing the user intent of operating the bicycle. The signal is interpreted by the control system as the user intent of starting the bicycle and, therefore, as a start signal of the motor control and of the power of the generator device. In absence of this starting signal, bicycle does not start to move.

The sensor 24 for detecting the user intent of operating bicycle can be variously shaped and arranged. For example it can coincide with the sensor 22 for detecting the pedaling speed. Alternatively it can comprise a sensor 22 for detecting the pedaling force applied to the pedaling assembly 6 by the user, as a torque sensor, or a force sensor, ore pressure sensors placed on the pedals 7, or strain gauges for measuring the bending of pedals 7. Alternatively, the pedaling force can be gathered from electric measurement made on the electric motor 8, where its features are known. Alternatively, the sensor 24 for detecting the user intent of operating bicycle can be a sensor independent of the others such as for example a motion sensor (such as an accelerometer) or a force sensor or a pressure sensor, placed for example on the handlebars 4. Alternatively the sensor 23 can be a start button for example.

With reference to the attached figures, it will now be described a method for controlling the pedal assisted bicycle according to the invention.

In the following description it is assumed that the storage device 10 is fully charged or that however it has a sufficient charge so that the bicycle can travel a certain distance. If the charge is not sufficient, it is possible to recharge the storage device, which is preferably connectable to external energy sources such as sockets, external batteries or similar.

Preferably, the method requires that before starting bicycle, the user sets the modes according to which he wants the bicycle to move. To this purpose, the method can comprise the preliminary steps of:

Setting the distance to travel d*; and/or

Setting the desired motion law: for example, the user can choose that the bicycle maintains a constant speed; alternatively it is possible to set a desired power of the motor or possibly the current to sent to the motor itself.

In order to make possible the above mentioned preliminary operations on startup, the bicycle 1 can comprise a control panel (not shown in Figures) preferably provided with a screen. For example, it is possible to provide a touch screen type screen, whereby it is also possible to provide commands to the control system.

Preferably, the bicycle 1 does not start as long as the control system does not detect the signal representing the user intent of operating bicycle, previously defined originated by the sensor 24. To this purpose the method comprises a step of detecting the presence or absence of such a signal representing the user intent of operating bicycle at the start of the bicycle itself. Depending on whether this signal is detected or not we have that:

If the signal is detected, the control method is started, in particular the control of the power required to the generator device (Wgen) and the power required to the motor (Wmot) are started;

Vice-versa, if the signal is not detected, the power required to the generator device Wgen and the power required to the generator device are maintained void and therefore the bicycle does not start. Alternatively, the power required to the generator device can be maintained equal to a predetermined minimum value Wgen*, so as to ensure a minimum resistance to pedal.

Once the signal representing the intent of operating bicycle is received by the control system, the control method is started.

Initially considering the situation in which the user pedals forward, i.e. he imparts a positive pedaling speed and he does not use the brakes, the method involves the following steps of:

Detecting the signal representing the heartbeat originated from the heartbeat sensor;

Determining the power required to the generator device Wgen in function of the signal representing the heartbeat;

Sending to the generator device a control signal representing the power required to the generator device (Wgen).

The modalities with which the power required to the generator device can be determined have been exposed previously and are based on the detection of the user's heartbeat.

In particular, according to a possible embodiment, determining the power required to the generator device comprises the following steps of:

Comparing the predetermined heartbeat profile with the heartbeat profile detected by the heartbeat sensor;
Making a closed-loop control of the error between the predetermined heartbeat profile and the heartbeat profile detected by the heartbeat sensor;
Sending to the generator device 9 a control signal representing the power required to the generator device Wgen.

The closed-loop control above described as mentioned earlier, can be done by controllers P, PD, PI, PID or other controllers, such as for example fuzzy logic controllers.

Preferably, the determination of the power required to the generator device comprises a step of maintaining the electric power required to the generator device (Wgen) below a predetermined maximum power value. The previously mentioned filter of the module for controlling the power required to the generator device can perform this step. In this way it is possible to avoid the peaks of the power required to the generator device and therefore also the peaks of effort by the user.

The power required to the generator device determined in the above mentioned modalities, based on the heartbeat monitoring, can be corrected in various ways.

According to a possible embodiment, the step of determining the power required to the generator device comprises the following steps of:

Detecting a signal representing the available energy amount in the storage device, for example of the charge of the batteries;
Determining the distance traveled by bicycle compared to a preset maximum distance that has to be traveled by the bicycle. Such a determination can be carried out, for example, through the previously mentioned sensor 25 for detecting the displacement of the bicycle;
Comparing the available energy amount in the storage device with a predetermined profile of the available energy amount as function of the distance traveled by the bicycle and of the preset maximum distance. These steps have been described with reference to FIG. 5;
Correcting the power required to the generator device Wgen in such a way that the energy amount accumulated in the storage device follows substantially the predetermined available energy amount staying within an upper and a lower limit respectively above and below the predetermined profile of the available energy amount.

According to a further possible embodiment, determining the power required to the generator device comprises also the following steps of:

Detecting a signal representing the bicycle speed;
Correcting the electric power required to the generator device based on such a signal representing the bicycle speed.

Figure 6:
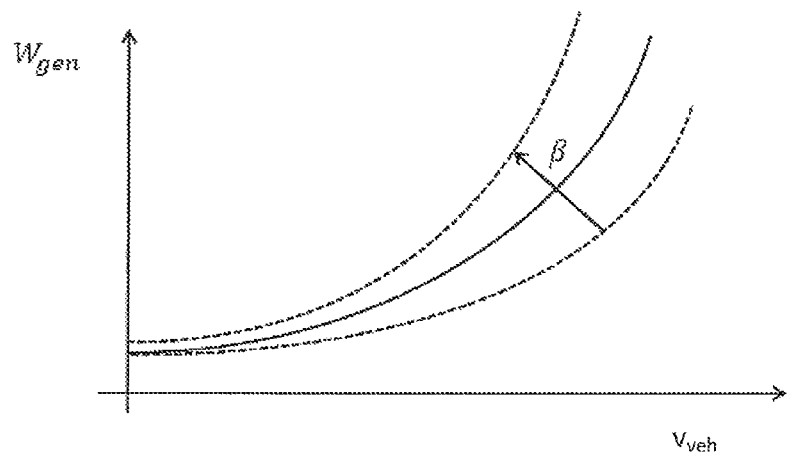
FIG. 6 è is a diagram illustrative of a method of controlling the bicycle according to a further possible embodiment.

This situation is previously described with reference to FIG. 6. These steps of the method have the function of simulating the aerodynamic resistance of the bicycle, for which it is possible, as already said, to correct the power required to the generator device with a term proportional to the detected bicycle speed to square.

The bicycle speed can also be used to further connect the power required to the generator device as a function of the bicycle inertia. In particular, it is possible, as already said, to correct the power required to the generator device with a term proportional to the speed variations between two successive instants.

According to a possible embodiment, the power required to the generator device can also be further corrected with a term, which is a fraction of the motor power. To this purpose, the step of determining the power required to the generator device may comprise the following steps of:

Detecting the power requited to the motor Wmot;
Correcting the power required to the generator device with a term $\alpha$Wmot, which is a fraction of the power required to the motor detected.

According to a further possible embodiment, the determination of the power required to the generator device comprises also a step of detecting a signal representing the path slope along which the bicycle moves (in particular through the sensor for detecting the path slop 18), and a step of correcting the power required to the generator device (Wgen) based on such a signal representing the path slop. For example in presence of a hill, the power required to the generator device may be increased, while in presence of a downhill, the power required to the generator device may be reduced down to possibly be cancelled.

What has been said so far refers to the control of the power required to the generator device. The power required to the motor is controlled, instead, as a function of the motion law set by the user.

The method according to the invention provides the possibility to manage the power flows between the generator device, the electric motor and the storage device depending on the circumstances.

In particular, advantageously, the method of control comprises the following steps of:

Detecting a power required to the electric motor Wmot in such a way that the bicycle moves according to the predetermined motion law, for example set by the user, in terms of speed, or power, or current of the motor;
Comparing the so determined power required to the electric motor Wmot and the power required to the generator device Wgen calculated in the way previously said.

Based on the outcome of comparison between these two powers, the method provides a step of controlling the generator device and the storage device in the following ways:

If the power required to the motor Wmot is equal to the power required to the generator device Wgen, the power required to the generator device is completely supplied to electric motor;
If the power required to the motor Wmot is higher than the power required to the generator device Wgen, the power required to the generator device is completely supplied to the electric motor and the portion of the missing power is supplied to the electric motor from the storage device;
If the power required to the motor Wmot is less than the power required to the generator device (Wgen), the portion of the power required to the generator device equal to the power required to the motor is supplied to the electric motor and the portion of the power required to the generator device in excess is supplied to the storage device.

In this way it is ensured that if the introduced power is higher than necessary for operating bicycle, the power surplus is stored in the storage device. It is also ensured that if the power introduced by the user is instead insufficient, the lacking of power is supplied to the motor from the storage device. Of course this is only possible as long as the storage device has a remaining battery life.

What has been said so far, it is working when the user pedals with a positive pedaling speed and in absence of braking.

In order to distinguish the pedaling modalities by the user, the method comprises a step of detecting the signal representing the pedaling assembly speed, in particular by the pedaling speed sensor 22. If the detected speed is positive, the power required to the generator device Wgen and the power required to the motor Wmot are determined according to what has been said so far. If instead the pedaling assembly speed detected is negative or void, the power required to the generator device Wgen e and the power required to the motor Wmot are maintained void. In other words, if the user stops pedaling, the motor thrust exhausts and, therefore, the bicycle stops (if it is not downhill). Alternatively, the power required to the motor Wmot is maintained negative.

Finally, in order to distinguish the conditions of braking and of braking absence, the method according to the invention comprises a step of detecting the presence or absence of the signal representing the bicycle braking intent, in particular through the signal provided by the user's stopping intent sensor 21.

In absence of such a signal, the power required to the generator device Wgen and the power required to the motor Wmot are determined according to the ways said so far.

If instead the signal representing the braking intent of the user is detected, the electric motor acts as a generator and its electric power, which in this case is a resistance power, is supplied to the storage device, which is therefore recharged. The power required to the generator device Wgen in this case is preferably maintained equal to a predetermined value of the power required to the generator device Wgen*, so as to ensure in any case a resistance to pedaling, even if minimum.

The method of control as described continues until the desired distance d* is traveled or the storage device is not fully discharged. Alternatively, the method of control, as seen, stops when the user stops pedaling, which condition is detected by the sensor for detecting the pedaling speed 22.

Note that, in the present description and in the attached claims, the control system, as well as the elements indicated with the expression "module", can be implemented by hardware devices (for example control units), by software or by a combination of hardware and software.

From the description provided above, the skilled person will appreciate how the pedal assisted bicycle, as well as the method of its control according to the invention, make possible to maintain under control the user effort during pedaling. In fact, based on the detection of the user's heartbeat the effort, which the user must be meeting by acting on the power required to the generator device, is reduced or increased. The method of control also allows simulating the resistance condition you should be meeting with a normal bicycle, while maintaining controlled the user's heartbeat.

The bicycle so configured is structurally simple because it is without mechanical elements normally present in standard bicycles.

Furthermore, the system and the method of control described allow to realize energy flows optimized for energy saving purpose, thanks to which the sizes of the storage device, in particular of the batteries, can be contained.

Moreover, the optimized energy flows allow reducing the frequency with which the storage device must be recharged instead of what happens in pedal assisted bicycle according to the technical note.

To the description given above of the pedal assisted bicycle and of its method of control, the skilled person, in order to satisfy contingent specific requirement, can make numerous addictions, modifications ore replacement of elements with other elements functionally equivalent, without, however, departing from the scope of the attached claims.

The invention claimed is:

1. A pedal assisted bicycle comprising:
   first and second wheels,
   a pedaling assembly mechanically decoupled from said first and second wheels, by which a user can supply a pedaling power,
   an electric motor mechanically coupled to at least one of said first and second wheels capable of taking a motor power,
   a generator device adapted to generate a generator device electric power from said pedaling power, arranged in an energy exchange relationship with the pedaling assembly and the electric motor,
   an energy storage device arranged in an energy exchange relationship with said electric motor and generator device,
   a control system comprising a module for controlling the power required to the generator device to be supplied to the electric motor and/or to the storage device, and
   a heartbeat sensor adapted to generate a signal representing the heartbeat,
   wherein said module for controlling the electric power required to the generator device is operatively connected to the heartbeat sensor and is configured in order to determine the electric power required to the generator device as a function of said signal representing the heartbeat.

2. The pedal assisted bicycle according to claim 1, wherein said control system comprises a module for controlling the electric motor such that the bicycle moves according to predetermined motion laws, said control system being further configured for comparing the electric motor required power and the generator device required power and for driving the generator device and storage device so that:
   if the motor required power is equal to the generator device required power, the generator device required power is totally supplied to the electric motor;
   if the motor required power is greater than the generator device required power, the generator device required power is totally supplied to the electric motor and the portion of the lacking power is supplied to the electric motor by the storage device;
   if the motor required power is less than the generator device required power, the portion of the generator device required power equal to the motor required power is supplied to the electric motor, and the portion of the excessive generator device required power is supplied to the storage device.

3. The pedal assisted bicycle according to claim 1, wherein said module for controlling the generator device required power is configured for determining the generator device required electric power by performing a comparison between a predetermined heartbeat pattern and the heartbeat pattern detected by said heartbeat sensor, and by performing a closed-loop control of the error between said predetermined heartbeat pattern and said heartbeat pattern detected by said heartbeat sensor.

4. The pedal assisted bicycle according to claim 1, wherein said heartbeat sensor is connected to the control system according to a wireless mode.

5. The pedal assisted bicycle according to claim 1, wherein said module for controlling the generator device required power comprises one or more filters adapted to hold the generator device required electric power below a predetermined maximum power value.

6. The pedal assisted bicycle according to claim 1, wherein said control system comprises a module for determining the available energy amount in the storage device and a sensor for detecting the distance travelled by the bicycle, operatively connected to the module for controlling the generator device required power, wherein said module for controlling the generator device required power is configured for determining the generator device required electric power as a function also of the available energy amount in said storage device and of the distance travelled by the bicycle with respect to a preset maximum distance.

7. The pedal assisted bicycle according to claim 1, comprising a sensor for detecting the bicycle speed adapted to generate a signal representing the bicycle speed, said module for controlling the generator device required power being operatively connected to said bicycle speed detecting sensor and being configured for determining the generator device required electric power as a function also of said bicycle speed representing signal.

8. The pedal assisted bicycle according to claim 1, comprising a sensor for detecting the slope of the path along which the bicycle is running, adapted to generate a signal representing the path slope, said module for controlling the generator device required power being operatively connected to the path slope detecting sensor and being configured for determining the generator device required electric power as a function also of said path slope representing signal.

9. The pedal assisted bicycle according to claim 1, comprising a braking device and a sensor for detecting the braking intent of the user, associated to the braking device, adapted to generate a signal representing the braking intent when the braking device is operated, said control system being operatively connected to the braking intent detecting sensor and being configured for determining the generator device required power and/or the electric motor required power as a function also of said braking intent representing signal.

10. The pedal assisted bicycle according to claim 1, comprising a sensor for detecting the pedaling assembly speed, adapted to generate a signal representing the pedaling speed, said control system being operatively connected to the pedaling assembly speed detecting sensor and being configured for determining the generator device required power and/or the electric motor required power as a function also of said signal representing the pedaling speed.

11. The pedal assisted bicycle according to claim 1, comprising a sensor for detecting the intent of the user of operating the bicycle, adapted to generate a signal representing the bicycle operating intent, said control system being operatively connected to the sensor for detecting the user intent of operating the bicycle and being configured in order to determine the generator device required power and/or the electric motor required power as a function of said signal representing the intent of operating the bicycle.

12. The pedal assisted bicycle according to claim 1, wherein said electric motor is adapted to operate as an electric generator in order to recover kinetic energy during the bicycle braking and/or when the bicycle runs along a downhill stretch and supply it to the storage device.

13. A method of controlling a pedal assisted bicycle which comprises first and a second wheels; a pedaling assembly mechanically decoupled from said first and second wheels by which the user can supply a pedaling power; an electric motor mechanically coupled to at least one of said first and second wheels capable of taking a motor power; a generator device adapted to generate an electric generator device power from said pedaling power, arranged in an energy exchange relationship with the pedaling assembly and electric motor; an energy storage device arranged in an energy exchange relationship with said electric motor and generator device; and a heartbeat sensor adapted to generate a signal representing the heartbeat, said method comprising:
  detecting the heartbeat-representing signal;
  determining the generator device required power as a function of said heartbeat representing signal; and
  supplying to the generator device a command signal representing the generator device required power.

14. The method according to claim 13, further comprising:
  determining an electric motor required power such that the bicycle moves according to a predetermined motion law;
  comparing said electric motor required power and generator device required power;
  driving the generator device and storage device so that:
    if the motor required power is equal to the generator device required power, the generator device required power is totally supplied to the electric motor,
    if the motor required power is greater than the generator device required power, the generator device required power is totally supplied to the electric motor and the portion of the lacking power is supplied to the electric motor by the storage device,
    if the motor required power is less than the generator device required power, the portion of the generator device required power equal to the motor required power is supplied to the electric motor, and the portion of the excessive generator device required power is supplied to the storage device.

15. The method according to claim 13, wherein the step of determining the generator device required power further comprises:
  performing a comparison between a predetermined heartbeat pattern and heartbeat pattern detected by said heartbeat sensor from said heartbeat representing signal;
  performing a closed-loop control of the error between said predetermined heartbeat pattern and said heartbeat pattern detected by the heartbeat sensor; and
  determining the generator device required power as a function of said error between the predetermined heartbeat pattern and the heartbeat pattern detected by the heartbeat sensor.

16. The method according to claim 13, wherein the step of determining the generator device required power further comprises holding the generator device required electric power below a predetermined maximum power value.

17. The method according to claim 13, wherein the step of determining the generator device required power further comprises:
  detecting a signal representing the available energy amount in the storage device;
  determining the distance travelled by the bicycle with respect to a preset maximum distance;
  detecting the available energy amount in the storage device;
  comparing the available energy amount in the storage device with a predetermined pattern of the available energy amount as a function of the bicycle travelled distance and said preset maximum distance; and
  correcting the generator device required power so that the energy amount stored in the storage device substantially follows said predetermined pattern of the available energy amount in order to remain between an upper and lower limits respectively above and below said predetermined pattern of the available energy amount.

18. The method according to claim 13, wherein the step of determining the generator device required power further comprises detecting a signal representing the bicycle speed and correcting the generator device required electric power as a function of said bicycle speed representing signal.

19. The method according to claim 13, wherein the step of determining the generator device required power further comprises:
   detecting a signal representing the path slope along which the bicycle is running; and
   correcting the generator device required power as a function of said path slope representing signal.

20. The method according to claim 13, comprising detecting a signal representing the pedaling assembly speed, so that:
   if the detected pedaling assembly speed is positive, the generator device required power and the motor required power are determined according to the method of claim 13;
   if the detected pedaling assembly speed is negative or zero, the generator device required power is zero and the motor required power is zero or negative.

21. The method according to claim 13, comprising detecting the presence or absence of a signal representing the bicycle braking intent of a user so that:
   in the presence of said signal representing the bicycle braking intent, the electric motor acts as a generator and the associated electric power is supplied to the storage device, and the generator device required power is kept equal to a predetermined value of the generator device required power;
   in the absence of such signal representing the bicycle braking intent, the generator device required power and motor required power are determined according to the method of claim 13.

22. The method according to claim 13, comprising detecting the presence or absence of a signal representing the user intent of operating the bicycle at the starting of the same, such that:
   in the presence of said signal representing the user intent of operating the bicycle, the generator device required power and motor required power are determined according to the method of claim 13;
   in the absence of said signal representing the user intent of operating the bicycle, the generator device required power is zero or equal to a predetermined value of the generator device required power, and the motor required power is zero so that the bicycle does not start.

* * * * *